United States Patent [19]

Bito

[11] Patent Number: 4,883,819

[45] Date of Patent: Nov. 28, 1989

[54] USE OF A, B AND C PROSTAGLANDINS AND DERIVATIVES THEREOF TO TREAT OCULAR HYPERTENSION AND GLAUCOMA

[75] Inventor: Laszlo Z. Bito, New York, N.Y.

[73] Assignee: The Trustees of Columbia University in the City of New York, New York, N.Y.

[21] Appl. No.: 22,046

[22] Filed: Mar. 5, 1987

Related U.S. Application Data

[63] Continuation-in-part of Ser. No. 892,387, Jul. 31, 1986, abandoned, which is a continuation-in-part of Ser. No. 839,056, Mar. 13, 1986, abandoned.

[51] Int. Cl.$^4$ .................... A61K 37/08; A61K 31/215
[52] U.S. Cl. .................... 514/573; 514/530; 514/913
[58] Field of Search .................... 514/530, 573, 913

[56] References Cited

U.S. PATENT DOCUMENTS

| | | | |
|---|---|---|---|
| 4,004,027 | 1/1977 | Lippmann et al. | 514/573 |
| 4,070,482 | 1/1978 | Lippmann et al. | 514/573 |
| 4,097,496 | 6/1978 | Babej et al. | 514/530 |
| 4,112,225 | 9/1978 | Holland et al. | 549/422 |
| 4,311,707 | 1/1982 | Birnbaum et al. | 514/573 |
| 4,564,637 | 1/1986 | Schachar | 514/573 |
| 4,599,353 | 7/1986 | Bito | 514/530 |

OTHER PUBLICATIONS

Chemistry, Biochemistry & Pharmaeological Acitivity of Prostanoids, pp. 1 & 4, 1978, Horton.
Chem. Abst., 71:120122(a), (1969) Beitch et al.
Chem. Abst., 78:80097(k) (1973), Nakano et al.
Chem. Abst., 80:44231(g) (1974), Chiang.
Chem. Abst., 81:21424(d) (1974), Chiang.
Chem. Abst., 81:45653(d) (1974), Masuda et al.
Chem. Abst. 102:161111(b) (1985), Trzeciakowski et al.
Beitch et al., The Effects of Prostaglandins on the Intraocular Pressure of the Rabbit, Br. J. Pharmac, 37, 158-167 (1969).
Nakano et al., Effects of Prostaglandins E1, E2, A1, A2 and F2 on Canine Carotid Arterial Blood Flow, Cerebrospinal Fluid Pressure, and Intraocular Pressure, J. Neurosurg, 38, 32-39 (1973).
Chiang, Effects of Epinephrine and Progesterone on the Ocular Hypertensive Response to Intravenous Infusion of Prostaglandin A2, Prost. 4(3), 415-419 (1973).
Chiang, Effects of Intravenous Infusions of Histamine 5-Hydroxytryptamine, Bradykinin and Prostaglandins on Intraocular Pressure, Arch. int. Pharmacodyn, 207, 131-138 (1974).
Masuda et al., Effects of Prostaglandins on Inflow and Outflow of the Aqueous Humor in Rabbits, Jap. J. Opthalmol, 17(4), 300-309 (1974).
Trjeciakowski et al., Effects of Prostaglandins on Intraocular Pressure Recovery Rate in Rabbits, Prest. 29(3), 497-510 (1985).

*Primary Examiner*—Douglas W. Robinson
*Assistant Examiner*—Zohreh Fay
*Attorney, Agent, or Firm*—John P. White

[57] ABSTRACT

This invention provides a method for treating hypertension or glaucoma in a subject's eye which comprises contacting the surface of the eye with an effective intraocular pressure reducing amount of one or more prostaglandins selected from the group consisting of prostaglandin A (PGA), prostaglandin B (PGB), prostaglandin C (PGC), derivatives of PGA, PGB, and PGC, conjugates of PGA and conjugated derivatives of PGA, so as to reduce the intraocular pressure of the eye and maintain such reduced intraocular pressure. Also provided is a composition for topical treatment of hypertension or glaucoma in the eye of a subject which comprises an effective intraocular pressure reducing amount of one or more prostaglandins selected from the group consisting of PGA, PGB and PGC, derivatives of PGA, PGB and PGC and conjugates of PGA and an opthalmically compatible carrier.

13 Claims, 15 Drawing Sheets

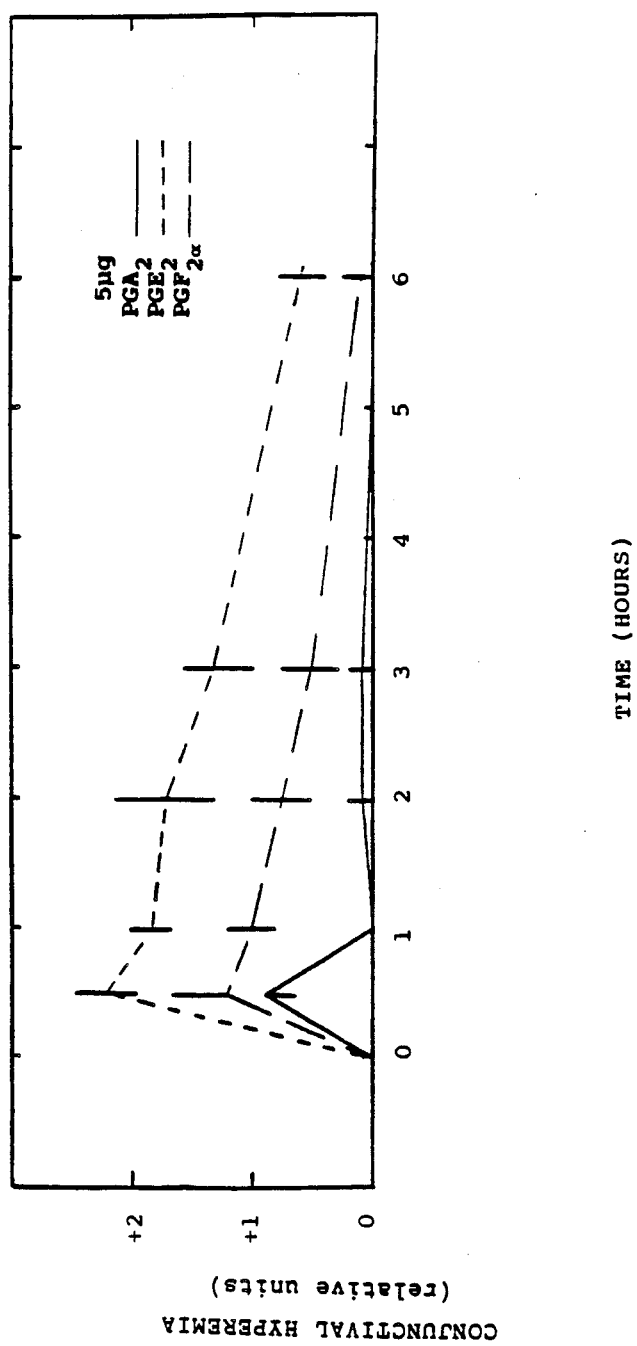

Figure 9A
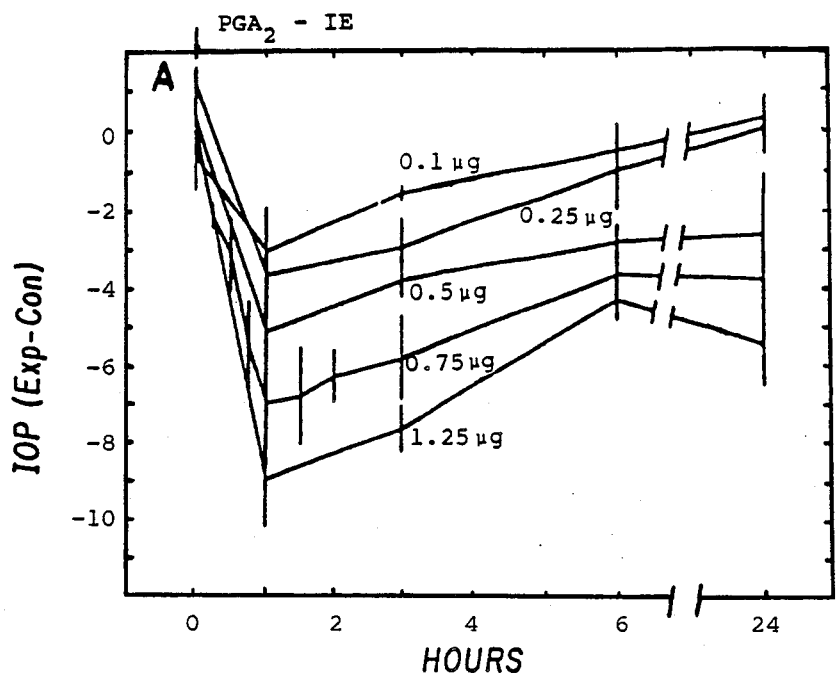
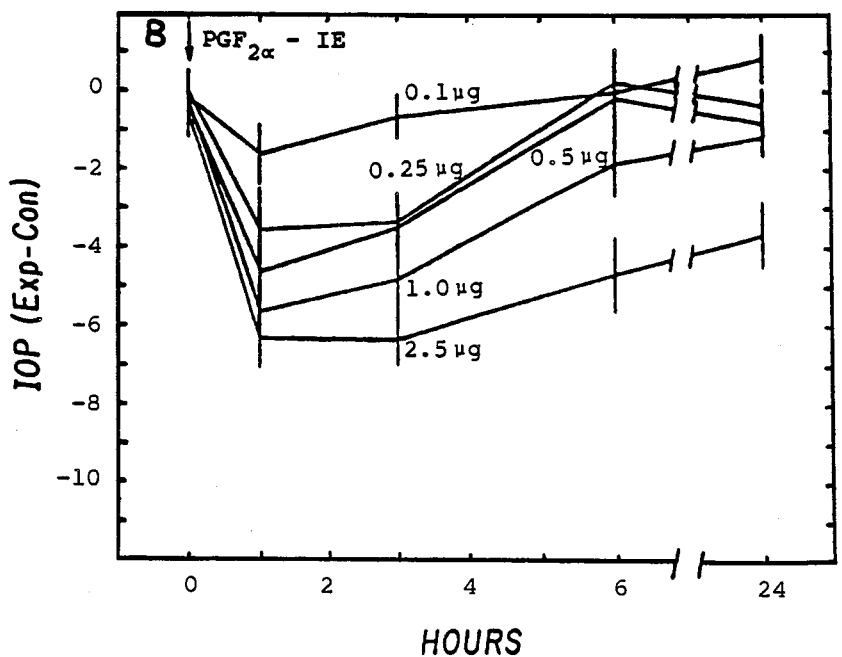
Figure 9B

USE OF A, B AND C PROSTAGLANDINS AND DERIVATIVES THEREOF TO TREAT OCULAR HYPERTENSION AND GLAUCOMA

This invention was made with government support under grant numbers EY00333 and EY00402 from the National Institutes of Health, United States Department of Health and Human Services. The U.S. Government has certain rights in this invention.

BACKGROUND OF THE INVENTION

This application is a continuation-in-part of U.S. Ser. No. 892,387, filed July 31, 1986, now abandoned, which is a continuation-in-part of U.S. Ser. No. 839,056, filed Mar. 13, 1986, now abandoned the contents both of which are hereby incorporated by reference into the present application.

Throughout this application various publications are referenced by numbers within parentheses. Full citations for these publications may be found at the end of the specification immediately preceding the claims. The disclosures of these publications, in their entireties, are hereby incorporated by reference into this application in order to more fully describe the state of the art to which this invention pertains.

Glaucoma, an eye disorder afflicting various mammals, including primates, is characterized by increased intraocular pressure (ocular hypertension). In man, such ocular hypertension results from an imbalance between the fate of secretion of aqueous humor by the ciliary epithelium into the posterior chamber of the eye and the resistance to flow or drainage of the aqueous humor from the anterior and posterior chambers, primarily via the canal of Schlemm. It is generally believed that increased outflow resistance due to obstruction of aqueous humor drainage routes is the primary cause of the imbalance.

Chronic glaucoma typically results in slow, progressive loss of visual fields and, if not controlled, ultimately in blindness. Initial treatment usually involves topical application of agonists or antagonists of autonomic neuroeffectors, particularly pilocarpine or timolol. If treatment with such topically applied drugs is not effective, systemic administration of carbonic anhydrase inhibitors may be employed. If such approaches are unsuccessful, the glaucoma may have to be treated by surgery.

Eicosanoids and their derivatives include numerous biologically useful compounds. For example, the prostaglandin (PG) group, naturally occurring cyclic fatty acids, is known to possess diverse biological activities. Originally isolated as lipid-soluble extracts from sheep seminal vesicles and human seminal fluid, prostaglandins have been found to be produced by most mammalian tissues.

Activities of different prostaglandins include stimulation of smooth muscle, dilation of small arteries, bronchial dilation, lowering of blood pressure, inhibition of gastric secretion, lipolysis and platelet aggregation, and induction of labor, abortion and menstruation.

It has previously been believed that administration of PG, particularly $PGE_2$, increases intraocular pressure based primarily upon results of studies involving intracameral administration into eyes of rabbits and some other mammals.

More recently, the primary prostaglandins (PGs), such as $PGE_2$, $PGF_{2\alpha}$ and $PGD_2$, have been shown to reduce intraocular pressure (IOP) in the cat and rhesus monkey with minimal side effects (3,4,11). However, relatively high concentrations of these eicosanoids had to be used, since the cornea is quite impermeable to these organic acids (2). Esterification of these prostaglandins was found to greatly improve the ocular hypotensive potency of $PGF_{2\alpha}$ to the point where amounts in the range of 1–5 microgram per application of different $PGF_{2\alpha}$ derivatives were found to cause a significant reduction of IOP (5). The increase in ocular hypotensive potency of the esters could be correlated with their increased penetration into the anterior chamber. See also, copending, coassigned U.S. patent application Ser. No. 374,165, filed May 3, 1982, now U.S. Pat. No. 4,599,353 issued July 8, 1986, the contents of which are hereby incorporated by reference into this application.

Several disclosures in the literature pertain to the effect on intraocular pressure of compositions containing PGAs and PGBs. Nakno et al. (10) disclose the intraarterial or intravenous injection of 1–100 micrograms/ml $PGA_1$ or $PGA_2$ in sodium chloride solutions. Nakano et al concluded that PGA used in this manner increases intraocular pressure in the dog. Trzeciakowski et al. (12) studied the effect of topical application of $PGA_2$ and $PGB_2$ on recovery of intraocular pressure in rabbits in which intraocular pressure had been artificially lowered. They concluded that $PGA_2$ and $PGB_2$ application counteracted the IOP lowering effect, produced by hypertonic saline injection, and effectively increased intraocular pressure.

Chiang (6) studied the effect of the intravenous infusion of $PGA_2$ on intraocular pressure. $PGA_2$ in a sodium carbonate/balanced salt solution consistently caused an elevated intraocular pressure. Finally, in Beitch and Eakins (1), intracameral injection of $PGA_1$ in a sodium chloride solution was found to produce a large, sustained increase in intraocular pressure. In this study, a marked decrease in response to repeated injection was observed.

The above-cited disclosures consistently teach away from the invention described herein. Topical application of PGs in the compositions of this invention produces a sustained lowering effect on intraocular pressure.

The experiments set forth herein establish that when applied topically to the eye in an appropriate formulation the free acid forms of $PGA_1$, $PGA_2$, $PGB_1$ and $PGB_2$ exhibit ocular hypotensive effects that are unexpectedly greater in magnitude or duration, or both, at comparable doses, than the effects observed with free acid forms of previously tested primary prostaglandins and other eicosanoids. The experiments also establish that the duration of conjunctival hyperemia induced by topical application of the free acid forms of PGAs and PGBs is shorter than that induced by topical application of identical doses or other PGs. Together these experiments demonstrate the unexpected therapeutic advantage of PGAs and PGBs in reducing intraocular pressure as compared with previously tested primary prostaglandins and other eicosanoids.

Experiments not disclosed herein demonstrate that $PGA_2$ in the free acid form penetrates the cornea more readily than $PGF_{2\alpha}$ in the free acid form. In addition, experiments set forth herein establish that significant intraocular pressure reductions may be achieved with lower doses of aliphatic esters at the 1-position of $PGA_2$, e.g., $PGA_2$-1-isopropyl ester, than may be achieved with the less lipid-soluble PGA$_2$ free acid, or with any other ocular hypotensive agent.

SUMMARY OF THE INVENTION

A method for treating hypertension or glaucoma in a subject's eye comprises contacting the surface of the eye with an effective intraocular pressure reducing amount of one or more prostaglandins selected from the group consisting of prostaglandin A (PGA), prostaglandin B (PGB), prostaglandin C (PGC), derivatives of PGA, PGB and PGC, conjugates of PGA and conjugated derivatives of PGA. As used herein, PGA means one or more of PGA$_1$, PGA$_2$ or PGA$_3$; PGB means one or more of PGB$_1$, PGB$_2$ or PGB$_3$; PGC means one or more of PGC$_1$, PGC$_2$ or PGC$_3$; and derivatives include esters of these PGs.

Suitable subjects include primates including man and other animals, particularly domesticated animals such as cats and dogs.

The effective amount of PGA, PGA derivative or PGA conjugate is in the range from about 0.1 microgram to about 100 micrograms, particularly from about 0.1 microgram to about 50 micrograms.

The effective amount of PGB or PGB derivative is in the range from about 0.1 microgram to about 100 micrograms, particularly from about 0.1 microgram to about 50 micrograms.

The effective amount of PGC or PGC derivative is in the range from about 0.1 microgram to about 100 micrograms, particularly from about 0.1 microgram to about 50 micrograms.

The invention further provides a composition for topical treatment of hypertension or glaucoma in the eye of a subject which comprises an effective intraocular pressure reducing amount of one or more prostaglandins selected from the group consisting of PGA, PGB, PGC, derivatives of PGA, PGB and PGC and conjugates of PGA and conjugated derivatives of PGA and an ophthalmically compatible carrier.

For liquid solutions, the effective amount comprises a dose of about 10 microliters to about 50 microliters of about 40 to about 4000 micrograms of prostaglandin per milliliter of liquid solution.

For ointments, the effective amount comprises about 10 milligrams to about 50 milligrams of ointment containing about 40 to about 4000 micrograms of prostaglandin per gram of ointment.

Postaglandins useful in this invention include PGA$_1$, PGA$_2$, PGA$_3$, PGB$_1$, PGB$_2$, PGB$_3$, PGC$_1$, PGC$_2$, PGC$_3$, and esters of these PGs, conjugates of PGAs and conjugated derivatives of PGA. Ophthalmically compatible carriers include aqueous solutions, ointments, and oils such as peanut oil or mineral oil.

BRIEF DESCRIPTION OF THE FIGURES

FIG. 9A. This figure shows the effect of topical application of PGA$_2$ isopropyl ester (PGA$_2$-IE) on IOP in the cat eye. Maximum IOP reduction consistently occured at 1 hr after the topical application of this drug and doses as low as 0.5 ug maintained significant IOP reduction at least up to 24 hr after application.

FIG. 9B. This figure shows the effect of topical application of PGF$_{2\alpha}$ isopropyl ester (PGF$_{2\alpha}$-IE) on IOP in the cat eye. The PGF$_{2\alpha}$-1-isopropyl ester at a dose of 1 μg yielded a maintained IOP reduction throughout the first day of its topical application and only at a dose of 2.5 μg was an IOP reduction at 24 hr observed that was comparable in magnitude to that observed after the topical application of 0.75 μg of PGA$_2$-IE.

DETAILED DESCRIPTION OF THE INVENTION

Figure 1:
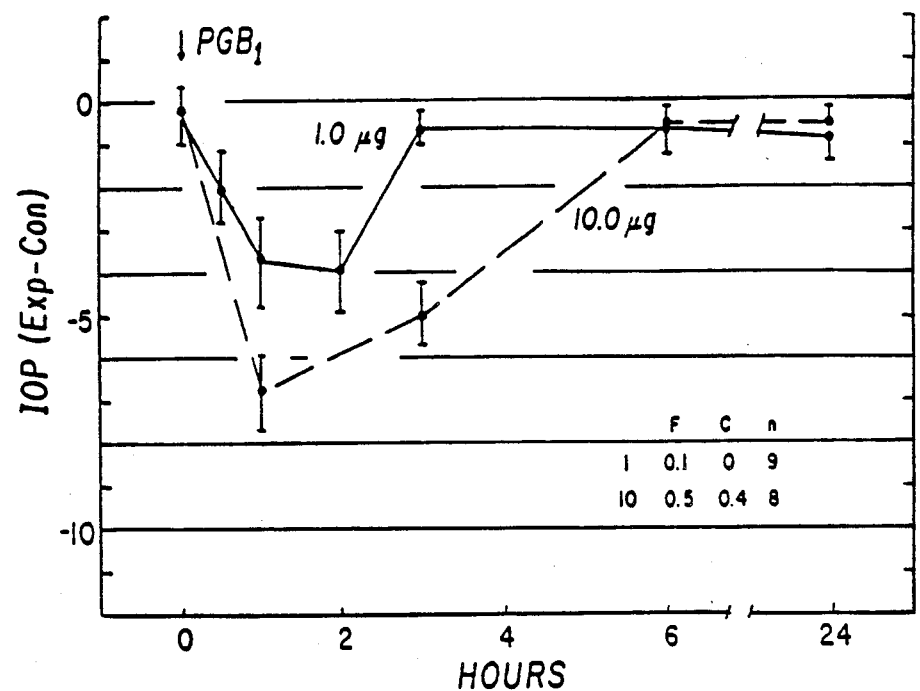
FIG. 1. This figure shows the effect of PGB$_1$ on IOP in the cat eye. Topical application of 1.0 microgram/eye gram/eye (———) or 10 micrograms/eye (— — —) caused a maximal IOP reduction of about 4mm Hg and about 7mm HG, respectively. Duration of the IOP reducing effect was extended to 6 hours with the higher dose. Relative values for observed flare (F) and cellular reaction (C) for each dose are shown at bottom right. Number of animals tested (n) is also given.

Prostaglandin A (PGA) is the class of compounds having the structural formula:

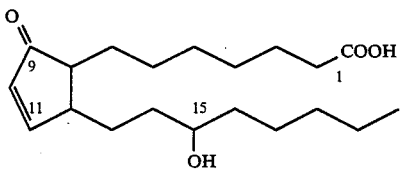

When the compound includes a double bond between carbon-13 and carbon-14 it is referred to as $PGA_1$. When the compound includes a second double bond between carbon-5 and carbon-6, it is referred to as $PGA_2$. When the compound includes a third double bond between carbon-17 and carbon-18, it is referred to as $PGA_3$. Numerous derivatives of the type A prostaglandins may be prepared by methods well known in the art.

In the practice of this invention derivatives of PGAs which comprise esters at the 1- position or at the 15-position or at both the 1-position and 15-position may be used. Of particular interest are aliphatic esters, such as methyl, ethyl, propyl or isopropyl, or arylalkyl esters, such as benzyl, at the 1-position or 15-position, or both, and aliphatic diesters, or mixed aliphatic and arylalkyl diesters, at the 1-position and 15-position.

Further, conjugates of PGAs may be prepared by reacting PGAs with chemical agents at carbon-11. Of particular interest are sulphydryl conjugates prepared by reacting PGAs with cysteine or glutathione.

Prostaglandin B (PGB) is the class of compounds having the structural formula:

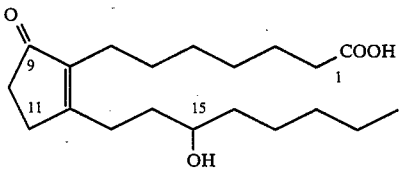

When the compound includes a double bond between the carbon-13 and carbon-14 it is referred to as $PGB_1$. When the compound includes a second double bond between carbon-5 and carbon-6, it is referred to as $PGB_2$. When the compound includes a third double bond between the carbon-17 and carbon-18, it is referred to as $PGB_3$. Numerous derivatives of the type B prostaglandins may be prepared by methods well known in the art.

In the practice of this invention derivatives of PGBs which comprise esters at the 1-position or at the 15-position or at both the 1-position and 15-position may be used. Of particular interest are aliphatic esters, such as methyl, ethyl, propyl or isopropyl, or arylalkyl esters, such as benzyl, at the 1-position or 15-position, or both, and aliphatic diesters, or mixed aliphatic and arylalkyl diesters, at the 1-position and 15-position.

Prostaglandin C (PGC) is the class of compounds having the structural formula:

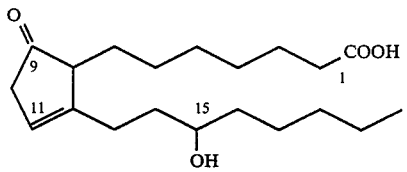

When the compound includes a double bond between carbon-13 and carbon-14 it is referred to as $PGC_1$. When the compound includes a second double bond between carbon-5 and carbon-6 it is referred to as $PGC_2$. When the compound includes a third double bond between carbon-17 and carbon-18, it is referred to as $PGC_3$. Numerous derivatives of the type C prostaglandins may be prepared by methods well known in the art.

In the practice of this invention derivatives of PGCs which comprise esters at the 1-position or at the 15-position or at both the 1-position and 15-position may be used. Of particular interest are aliphatic esters, such as methyl, ethyl, propyl or isopropyl, or arylalkyl esters, such as benzyl, at the 1-position or 15-position, or both, and aliphatic diesters, or mixed aliphatic and arylalkyl diesters, at the 1-position and 15- position.

A method for treating hypertension or glaucoma in a subject's eye is described. Suitable subjects include animals such as primates, e g. man, and domestic animals, e.g. dogs and cats. The method comprises contacting the surface of the eye with an effective intraocular pressure reducing amount of one or more prostaglandins selected from the group consisting of prostaglandin A (PGA), prostaglandin B (PGB), prostaglandin C (PGC), derivatives of PGA, PGB and PGC, conjugates of PGA and conjugated PGA derivatives, so as to reduce the intraocular pressure of the eye and maintain such reduced intraocular pressure.

The prostaglandins of this disclosure are one or more of $PGA_1$, $PGA_2$, $PGA_3$, $PGB_1$, $PGB_2$, $PGB_3$, $PGC_1$, $PGC_2$ or $PGC_3$.

Derivatives of the preferred embodiment include aliphatic esters and diesters and arylalkyl esters at the 1-position or the 15-position or at both the 1-position and 15-position of PGA, PGB or PGC. Aliphatic esters of the preferred embodiment are methyl, ethyl, propyl, isopropyl and the like. Preferred arylalkyl esters are benzyl esters at the 1-position or 15-position or both.

PGA conjugates of the preferred embodiment are sulphydryl conjugates of carbon-11, particularly those conjugates formed by the reaction of PGA or PGA derivaties with cysteine or glutathione.

Various regimens may be employed for treating hypertension or glaucoma in the subject's eye. In the preferred embodiment, PGA, PGA derivative and PGA conjugate treatment comprises contacting periodically, e.g. at least daily, the surface of the eye, e.g., the cornea, with an amount of the prostaglandin effective to reduce intraocular pressure and to maintain reduced intraocular pressure. The preferred treatment with PGB and PGC, and derivatives thereof, comprises contacting periodically, e.g., one to four times daily, the surface of the eye, e.g., the cornea, with an amount of the prostaglandin effective to reduce intraocular pressure and to maintain such reduced intraocular pressure.

Although a wide range in the amount of prostaglandin may be employed for the practice of the present invention, the preferred amount is from about 0.1 microgram to about 500 micrograms, specifically from about 0.1 microgram to about 50 micrograms.

Further disclosed is a composition for topical treatment of hypertension or glaucoma in the eye of a subject which comprises an effective intraocular pressure reducing amount of one or more prostaglandins selected from the group consisting of PGA, PGB, PGC, derivatives of PGA, PGB and PGC, conjugates of PGA and conjugated PGA derivatives and an ophthalmically compatible carrier.

The prostaglandins of this disclosure are one or more of $PGA_1$, $PGA_2$, $PGA_3$, $PGB_1$, $PGB_2$, $PGB_3$, $PGC_1$, $PGC_2$ or $PGC_3$.

Derivatives of the preferred embodiment include aliphatic esters and diesters and arylalkyl esters at the 1-position and 15-position or at both the 1-position and 15-position of PGA, PGB or PGC. Aliphatic esters of the preferred embodiment are methyl, ethyl, propyl, isopropyl and the like. Preferred arylalkyl esters are benzyl esters at the 1-position or 15-position, or both.

Ophthalmically compatible carriers which may be used in the practice of this invention include, but are not limited to, aqueous solutions, e.g. saline or isotonic solutions containing preservatives, oils, e.g., peanut oil or mineral oil, and ointments. Ointments of this invention are semisolid medicinal preparations having a hydrocarbon or oleaginous base. Ointments of the preferred embodiment include polyethylene-mineral oil ointments and the like.

The compositions of this invention are typically sterile and may desirably include additional components well known to those skilled in the art for use in such compositions. For example, the composition may also include preservatives, antioxidants, bacteriostats, stabilizing agents, solubilizing aids, colorants, emulsifiers and the like. Particularly when the PG is a PGC, the use of stabilizing agents may be necessary.

For liquid solutions, the effective amount comprises a dose of about 10 microliters to about 50 microliters of about 40 to about 4000 micrograms of prostaglandin per milliliter of liquid solution.

For ointments, the effective amount comprises about 10 milligram s to about 50 milligrams of ointment containing about 40 to about 4000 micrograms of prostaglandin per gram of ointment.

Also disclosed is a method for topically treating hypertension or glaucoma in a subject's eye which comprises contacting the surface of the eye with an effective amount of a composition of this invention.

In the preferred embodiment, contacting will be periodical, e.g., at least daily when the prostaglandin is PGA, and from one to four times daily when the prostaglandin is PGB or PGC.

This invention provides an improved method for the treatment of ocular hypertension or glaucoma. PGA, PGB and PGC not only decrease intraocular pressure at relatively low doses, but PGA in particular produces a long-lasting reduction of intraocular pressure. Further, the prostaglandins of this invention are notable for their limited iatrogenic effect. Specifically, they cause much less conjunctival hyperemia than do related compounds which lower intraocular pressure.

First Series of Experiments

The free acid forms of $PGA_1$, $A_2$, $B_1$ and $B_2$ were purchased from Cayman Chemical Company (Ann Arbor, Michigan) and made up in an ophthalmic vehicle solution (0.5% polysorbate 80 and 0.01% benzalkonium chloride in normal saline) by first dissolving 10 micrograms of the free acid in 25 microliters of ethanol and then adding 0.5 ml of the vehicle solution, yielding a PG concentration of 20 mg/ml. Further dilutions were made with the vehicle solution to obtain a concentration in the range of 40 to 4000 micrograms per ml with an ethanol concentration less than 3%. Twenty-five microliters of one of these solutions representing 1.0 to 500 micrograms of PG were applied topically to the cornea of one eye of each cat. The contralateral eye that served as a control received either the same volume of vehicle solution or remained untreated. Intraocular pressure was measured with an Alcon Applanation Pneumatonograph several times before drug application and at 1, 3, 6 and 24 hr, and in some cases also at 0.5 and 2.0 hr, thereafter. The same eye of each cat was not used for drug testing more than once every week and no cat was used more than twice a week for single dose testing. In some cases the same PG at the same concentration was applied once a day for several days.

Slit lamp examination of the eye was performed and the extent of flare and the presence of cells in the anterior chamber were evaluated prior to PG treatment and at 3, 6 and 24 hr after PG application. These responses were rated as previously described (3).

Results $PGB_1$ at a dose of 1.0 to 10.0 micrograms per eye causes a significant reduction of IOP (FIG. 1). The maximum average IOP reduction with the 1.0 microgram dose was about 4 mm Hg (mean 3.9±1; 9 eyes) from 1 to 2 hours after treatment but the IOP returned to essentially normal levels by 3 hz with the higher dose (10 micrograms/eye) the maximum average IOP reduction was significantly greater (mean 6.8±0.9 at 1 hour; 8 eyes; range 4–10 mm Hg) and the duration was slightly extended but again the IOP returned to essentially normal level by 6 hr (FIG. 1). This hypotensive effect was associated with minimal flare at either dose and a minimum cellular reaction at the higher dose. Cells or flare were not consistently observed after the topical application of 1.0 microgram of $PGB_1$.

Figure 2:
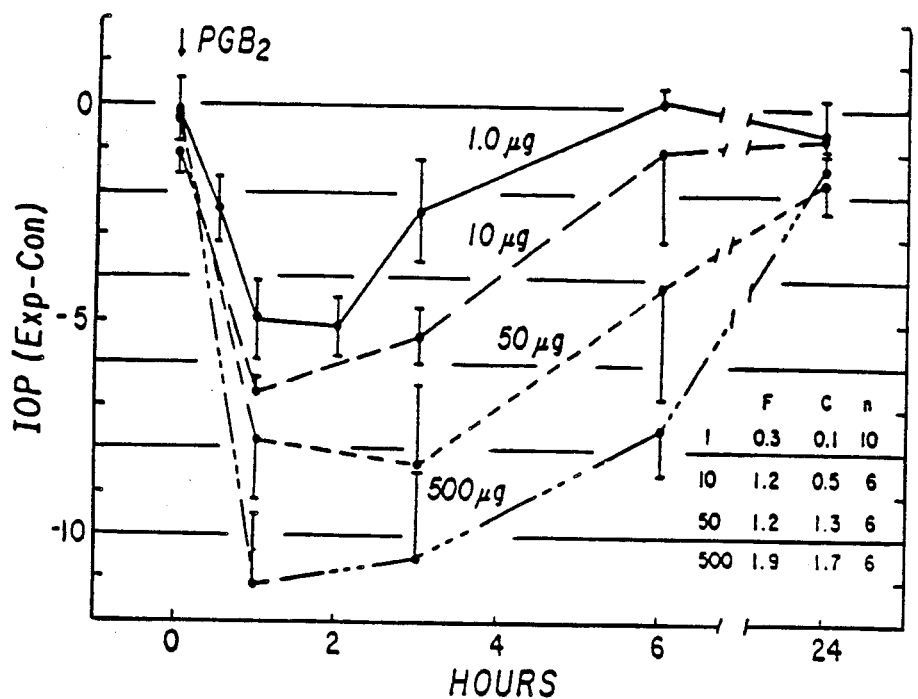
FIG. 2. This figure shows the effect of PGB$_2$ on IOP in the cat eye. Increasing the PGB$_2$ dose to 50 micrograms/eye and 500 micrograms/eye increases the extent and duration of the IOP reducing effect. Data for observed flare and cellular reaction are presented as in FIG. 1.

Similar responses were observed after the topical application of the same doses of $PGB_2$ (FIG. 2). Increasing the $PGB_2$ dose to 50 and 500 micrograms per eye increased the extent and the duration of the IOP lowering effect, but with neither dose was a significant reduction in IOP observed 24 hr after treatment. Some flare and cells were observed in at least some of the eyes after the topical application of any of these $PGB_2$ doses and the extent of these side effects was dose dependent.

Figure 3:
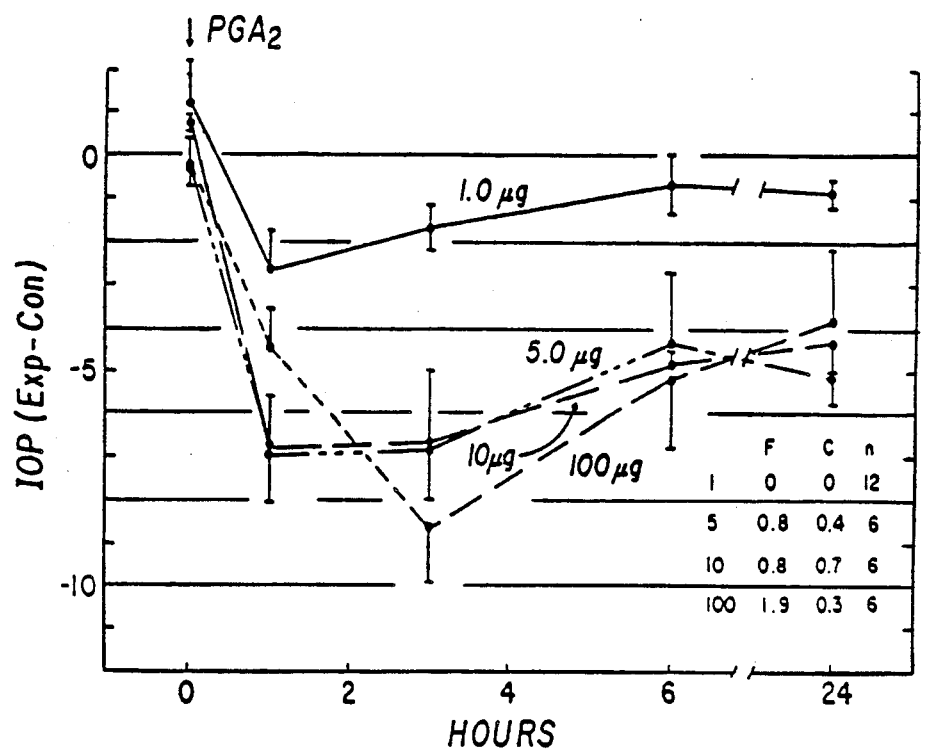
FIG. 3. This figure shows the effect of PGA$_2$ on IOP in the cat eye. As with PGB$_2$, increasing the PGA$_2$ dose results in increased extent and duration of the IOP reduction. Data for observed flare and cellular reaction are presented as in FIG. 1.
Figure 4:
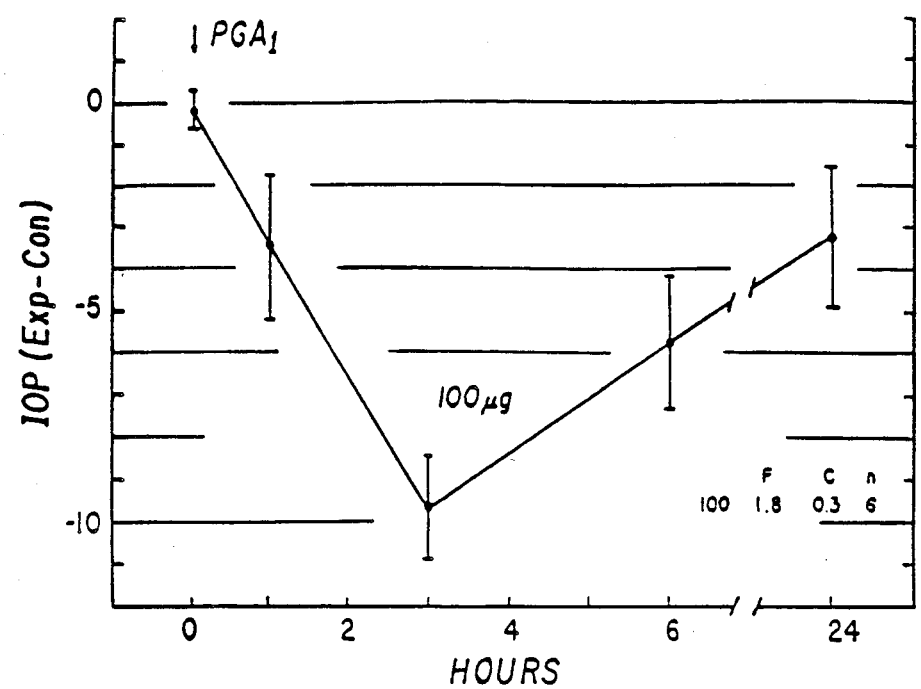
FIG. 4. This figure shows the effect of PGA$_1$ on IOP in the cat eye. At a dose of 100 micrograms/eye, PGA$_1$ caused a large reduction of 8mm Hg in IOP. Data for observed flare and cellular reaction are presented as in FIG. 1.

Significant IOP reduction was also obtained 1 hr after the topical application of as little as 1.0 microgram of $PGA_2$ per eye (FIG. 3). Topical application of 5, 10 or 100 micrograms yielded dose dependent reductions of IOP and these IOP reductions were also comparable to those obtained after the topical application of similar doses of $PGB_2$ (FIG. 2 vs. FIG. 3). However, in all three of the $PGA_2$ doses, the duration of IOP reduction was unexpectedly long, far exceeding that observed with primary PGs or with $PGB_2$. At 24 hr after the topical application of 5–100 micrograms of PGA2, the IOP was still reduced to a value 4-6 mm Hg below that of the contralateral control eyes. $PGA_1$ at a dose of 100 micrograms per eye also yielded a large reduction of IOP averaging over 8 mm by 3 hr after treatment (FIG. 4). This IOP reduction was similar in extent and duration to the ocular hypotensive response obtained with the same dose of $PGB_2$. These findings show that PGs of the A and B type are unexpectedly potent ocular hypotensive agents, and that the duration of the hypotensive effect of $PGA_2$ is unexpectedly long as compared to the duration of the ocular hypotension observed previously with the topical application of a single dose of primary PGs.

Figure 5:
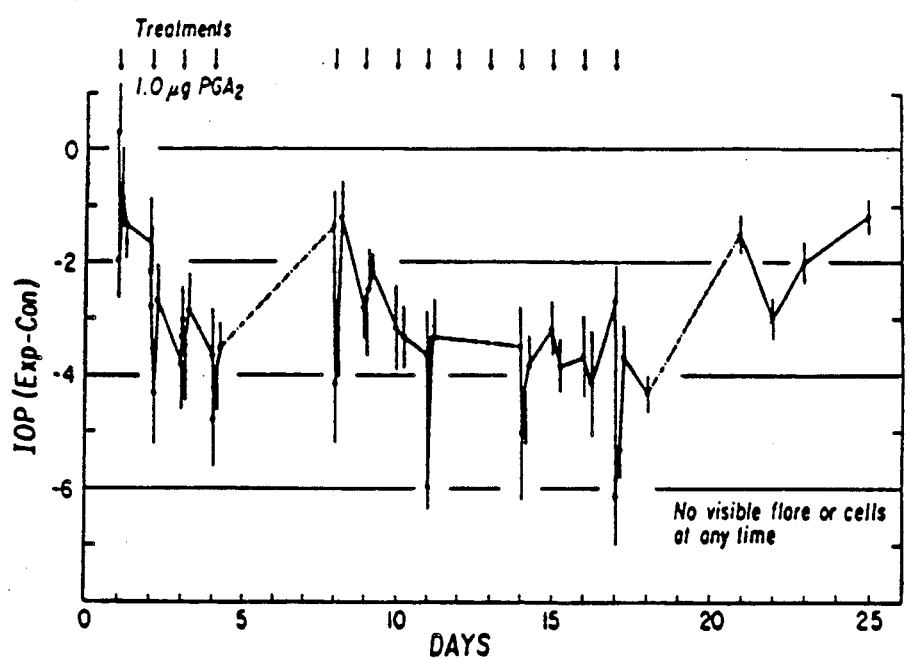
FIG. 5. This figure shows the effect of periodic application of PGA$_2$ on IOP in the cat eye. Periodic topical application of 1.0 microgram PGA$_2$/eye resulted is unexpectedly long IOP reduction. This figure demonstrates that there is no tachyphylaxis to the ocular hypotensive effect of PGA$_2$. No flare or cellular reaction was seen.

Repeated applications of $PGA_2$ at a dose of 1.0 microgram per eye resulted in a reduction in IOP demonstrating that there is no tachyphylaxis due to the ocular hypotensive effect of this PG (FIG. 5). In fact, during 4 days of daily $PGA_2$ application the IOP showed a gradual decline. When PG treatment was then suspended, the IOP of the previously treated eye remained low as compared to the contralateral control eye until 3 days after the last treatment. When treatment was then resumed for 10 consecutive days, the IOP again gradually decreased over a four-day period and remained at a low level as long as the daily treatment was continued. Although episodes of further decreases in IOP were seen within the first three hours after the application of each dose, the ocular hypotensive effect that was maintained over a 24-hr period after each treatment between 6 and 10 days of treatment was in the range of 3 to 4 mm Hg as compared to the contralateral control eyes. After a total of 14 $PGA_2$ applications over a period of 17 days, PG treatment was stopped. IOP then gradually increased, but even 7 days after the last treatment there was still some reduction in the IOP of the previously treated eyes as compared to the contralateral control eyes (FIG. 5). No cells or flare were visible in these eyes during the entire period of treatment with 1.0 microgram of $PGA_2$. Even with the higher doses of $PGA_2$ (5-10 micrograms per eye) the flare or cellular response observed was comparable to or less than that observed with the much higher doses of $PGF_2$ free acid that were previously shown to be required to yield a comparable reduction of IOP.

These experiments demonstrate that derived PGs of the A and B type have unexpectedly greater ocular hypotensive potency than the previously studied primary PGs. Furthermore, current findings demonstrate that PGs of the A type maintain a reduced IOP for a much longer period of time than primary PGs or their esters. It is concluded, therefore, that PGs of the A and B type, and especially of the A type, have distinct and unexpected therapeutic advantages over previously studied primary eicosanoids or their derivatives for the long-term treatment of chronic simple glaucoma.

Second Series of Experiments

It has been shown that during the course of daily treatment of cat eyes with $PGA_2$ at a dose of 1 microgram per treatment, the intraocular pressure (IOP) was significantly reduced, and that this reduction in IOP was not accompanied by observable flare or by cells in the anterior chamber. This is in contrast to previous studies on cats with ocular hypotensive doses of primary PGs or esters of $PGF_{2\alpha}$ that consistently cause some flare and cellular response (3, 5). In the human eye neither flare or cells were observed in the anterior chamber after topical application of a hypotensive dose of $PGF_{2\alpha}$, but a pronounced conjunctival hyperemia was evident in all eyes so treated (9). $PGF_{2\alpha}$ esters, that were shown in animal studies to be much more potent ocular hypotensive agents than the free acid or salt-form of $PGF_2$, were also found to cause conjunctival hyperemia of the human eye when used in much lower doses (1 to 10 micrograms) than the dose of $PGF_{2\alpha}$ used by Giuffre (9). It seems, therefore, that as far as the human eye is concerned, conjunctival hyperemia is a more important ocular side effect of some PGs than cells or flare. Therefore, when considering the therapeutic advantage of derived PGs over primary PGs or their esters, one must consider not only their ocular hypotensive potency but also their conjunctival hyperemic potency.

It is difficult or virtually impossible to study conjunctival hyperemia in the cat eye since the conjunctival surface is completely covered by the lids in this species, while in monkeys visualization of the conjunctival vasculature is greatly hindered by heavy pigmentation of the visible portion of the conjunctiva. The relative conjunctival hyperemic potency of PGs was, therefore, studied on rabbit eyes using doses of $PGA_2$, $PGE_2$ and $PGF_{2\alpha}$ which were shown to cause a significant IOP reduction in cats.

Figure 6B:
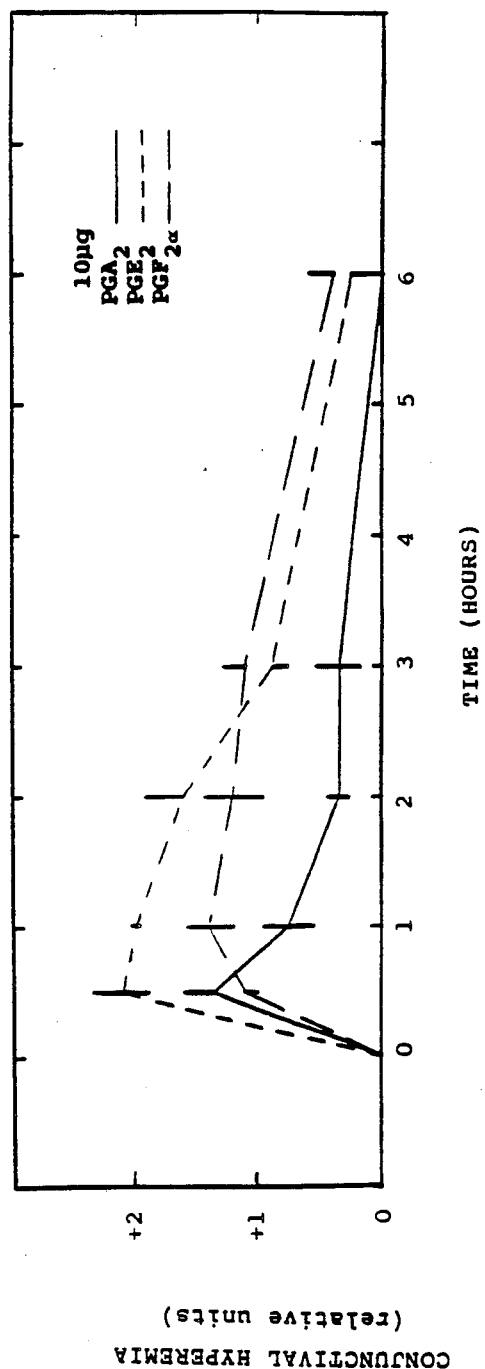
FIG. 6. Comparison of the time course and extent of the conjunctival hyperemic effect of PGA$_2$, PGE$_2$, and PGF$_{2\alpha}$ applied topically to the rabbit eye in 25 microliter volumes of ophthalmic vehicle solution described in the First Series of Experiments FIG. 7. Data showing the stability of a PGA$_2$ solution is presented. 1.0 microgram/eye doses of a PGA$_2$ solution freshly made (———), after 49 days (— — —) and after 126 days (———) were topically applied to a cat eye. IOP reduction was still effected by the 126 day old PGA$_2$ solution. No cells, flare or miosis were seen.

Topical application of 5 micrograms of $PGA_2$ in 25 microliters of a typical ophthalmic vehicle solution caused only a brief episode of moderate conjunctival hyperemia as compared to the extent and duration of the conjunctival hyperemia observed in eyes that were treated with an identical dose of $PGE_2$ or $PGF_{2\alpha}$ in identical vehicle solution (FIG. 6). While the maximum extent of the conjunctival hyperemia observed in $PGF_{2\alpha}$ a treated eyes was not significantly greater than that observed in $PGA_2$-treated eyes, the decline of hyperemia in $PGF_{2\alpha}$ treated eyes was very slow as compared to $PGA_2$ treated eyes. Eyes treated with identical doses of $PGE_2$ showed conjunctival hyperemic response much greater in maximal extent and much longer in duration than either the $PGA_2$ or $PGF_{2\alpha}$ treated eyes.

When the doses of these PGs were doubled (from 5 to 10 micrograms per eye), both the duration and the extent of the conjunctival hyperemic responses to $PGA_2$ and $PGF_{2\alpha}$, but not to $PGE_2$, were increased indicating that the response to the 5 micrograms of $PGE_2$ was already maximal. The maximum conjunctival hyperemic response induced by 10 micrograms of $PGA_2$ was also slightly greater in extent at 30 min than the response observed after the topical application of 5 micrograms of $PGA_2$. While this conjunctival hyperemia was also of longer duration than that observed after 5 micrograms of $PGA_2$, it showed a relatively rapid decline as compared to the conjunctival hyperemic response induced by the same dose of $PGF_{2\alpha}$ (FIG. 6). Similar results were obtained with $PGA_1$, $PGB_1$ and $PGB_2$. At a dose of 5 micrograms or 50 micrograms per eye, these PGs caused a conjunctival hyperemic response comparable to or less than the same doses of $PGF_{2\alpha}$ or $PGA_2$.

This study shows that while the conjunctival hyperemia induced by $PGF_{2\alpha}$ and $PGA_2$ are roughly comparable in extent, the duration of conjunctival hyperemia induced by $PGA_2$ is much shorter than that induced by $PGF_{2\alpha}$. Thus, $PGA_2$ has a therapeutic advantage over $PGF_{2\alpha}$. It should be pointed out that the therapeutic advantage of $PGA_2$ as compared to $PGF_{2\alpha}$ is much greater than is apparent from this comparison of the conjunctival hyperemic effects of these two drugs at the same doses, since $PGA_2$ was shown to have an ocular hypotensive effect at the dose range of 1-10 micrograms in cat eyes whereas the free acid of $PGF_{2\alpha}$ yields a similar reduction in IOP only at some 10-100 fold higher doses.

One must conclude therefore that $PGA_2$ has an unexpected therapeutic advantage for the treatment of ocular hypertension and glaucoma not only with regard to its more potent ocular hypotensive effects but also with regard to conjunctival hyperemia, an adverse ocular side effect that has been demonstrated to occur in humans after the topical application of hypotensive doses of $PGF_{2\alpha}$.

Third Series of Experiments

A description of the procedure used in making stock solutions of the derived prostaglandins is included in the First Series of Experiments. All solutions described below were applied topically in a volume of 25 microliters.

Stability of a $PGA_2$ solution in the current vehicle was tested over a period of 4 months. The initial stock solutions (0.2 mg/ml; 4 micrograms/25 microliters $PGA_2$ made up in the current vehicle) were stored in transparent polypropylene microcentrifuge tubes at room temperature with no protection from fluorescent room light or indirect sunlight. All tests of the hypotensive potency of $PGA_2$ were conducted by diluting an aliquot of the stock solution with the current vehicle to a concentration of 0.04 mg/ml equal to a dose of 1 microgram $PGA_2$/25 microliters.

Immediately following the preparation of a $PGA_2$ stock solution, an aliquot of the solution was diluted to yield a concentration of 0.04 mg/ml and 25 microliters of this dilution (1 microgram $PGA_2$) was applied topically to one eye of each of six cats. Intraocular pressure (IOP). aqueous humor flare and cellular invasion of the anterior chamber were monitored as previously described in the First Series of Experiments. The hypotensive efficacy of the stock $PGA_2$ solution was then retested at the same 1 microgram/eye dose after storage for 49 and 126 days.

Figure 7:
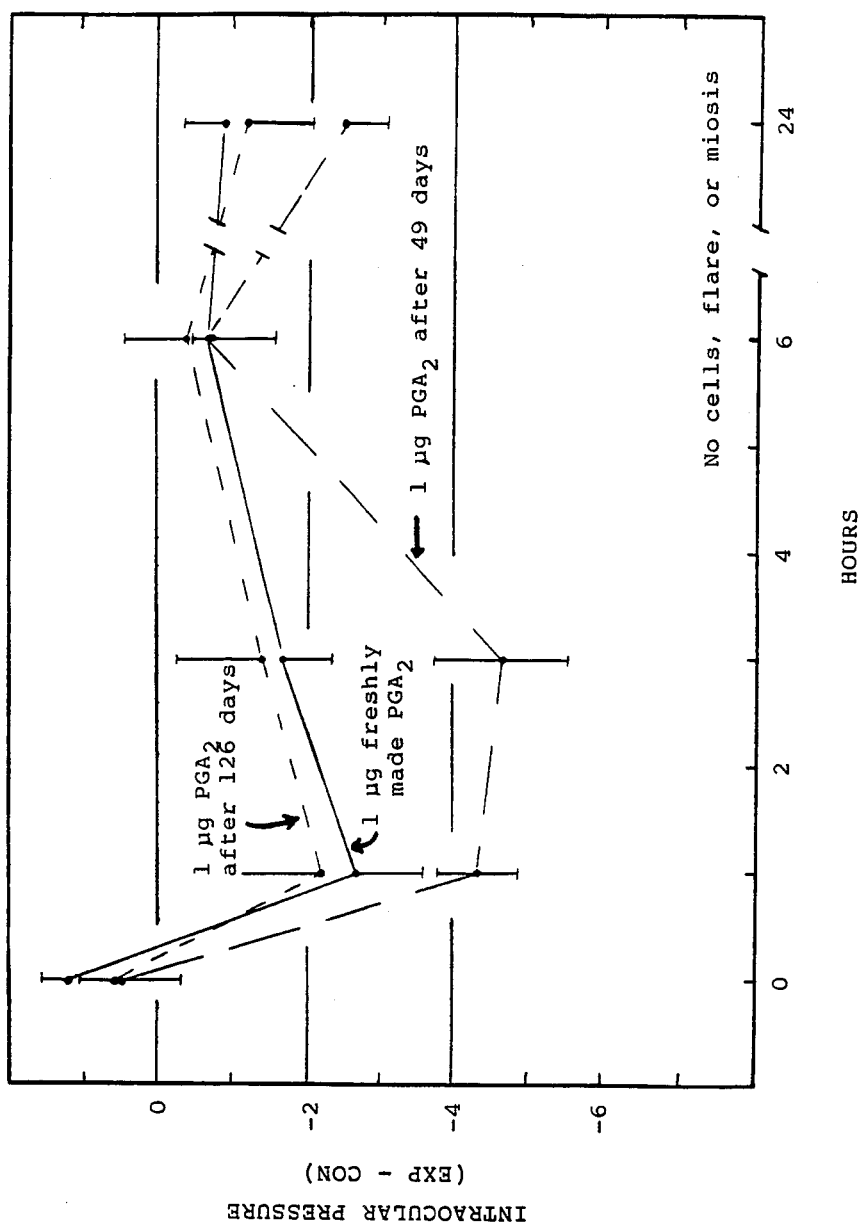

IOP reduction obtained after 49 days of storage was somewhat greater and more prolonged than the IOP reduction obtained with the fresh stock solution. However, at 126 days the response was not significantly different from that obtained initially (FIG. 7).

Figure 8A:
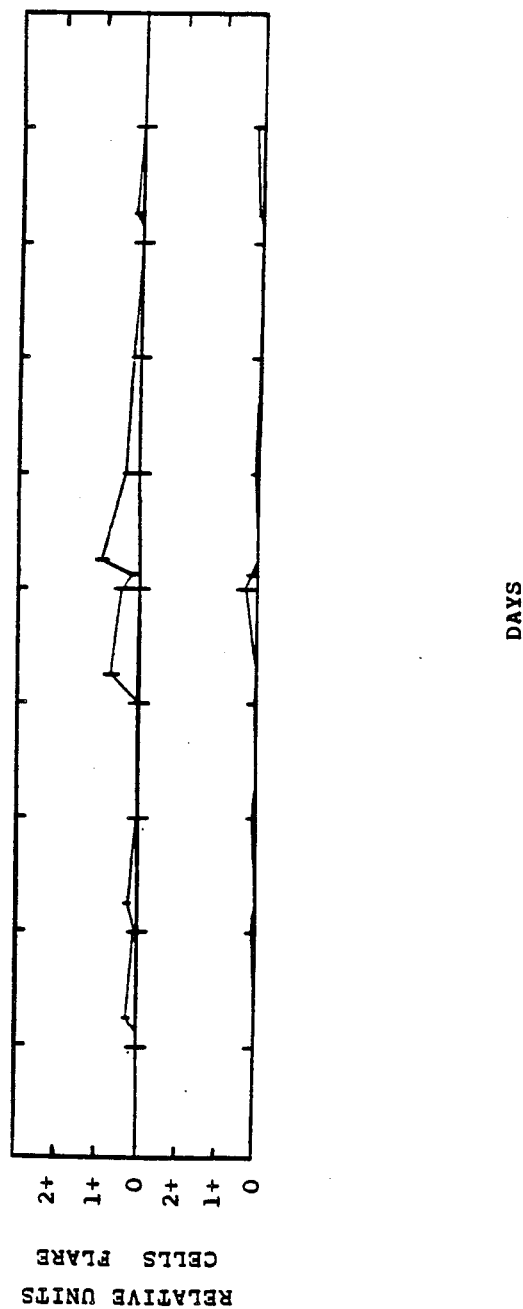
FIG. 8. Long term PGB$_2$ treatment regimen and its effect on IOP are shown. 5 micrograms/eye doses of PGB$_2$ were applied topically to the cat eye for eight consecutive days. Greatest IOP reduction was seen after fourth day (bottom graph). Little or no consistent flare (top graph) and little cellular reaction (middle graph) was observed.
Figure 8B:
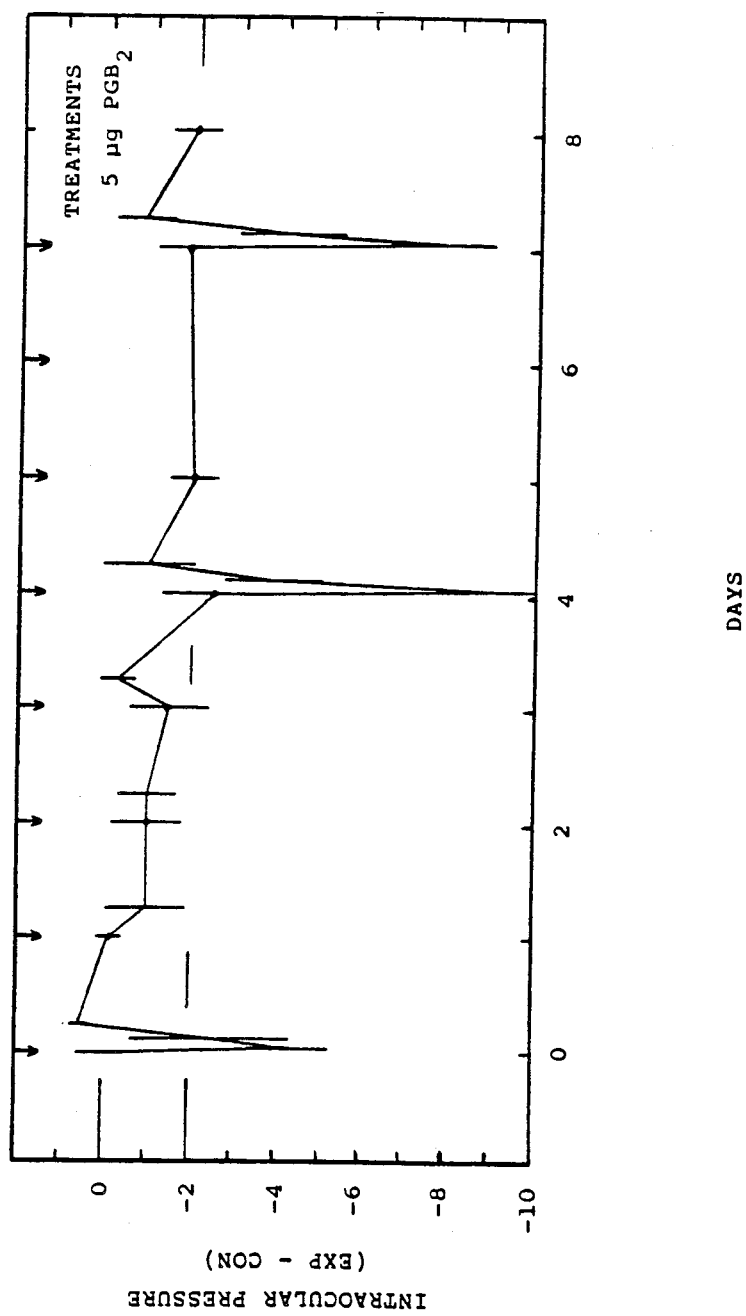

The hypotensive efficacy of a long-term $PGB_2$ treatment regimen was studied by topical application of 5 micrograms $PGB_2$ in 25 microliters of the current vehicle to one eye of each of six cats for eight consecutive days. IOP, aqueous humor flare and cellular invasion of the anterior chamber was monitored periodically on days 1, 5 and 8 and one or two IOP readings and observations were made on all other days except for day 7. Both the short-term (spike) IOP reduction and the maintained (24 hour) IOP reduction were greater after subsequent treatments than after the first treatment. The lowest IOP values were obtained after the fourth treatment (FIG. 8). There was a little or no consistant flare and an appreciable cellular response was observed in the anterior chamber of one eye only on day 5.

FOURTH SERIES OF EXPERIMENTS

Materials and Methods

Cats of either sex (1.5 to 3.0 kg) were trained to accept handling and periodic restraint required for biomicroscopic examination of their eyes and for tonometric IOP determinations. Only animals that were in good health and whose eyes showed no biomicroscopic signs of ocular inflammation were used.

In most single dose experiments, tonometry and slit-lamp examination of the eye to evaluate the extent of flare and the presence of cells in the anterior chamber was performed prior to PG treatment and at 3, 6, and 24 hr thereafter. Tonometry was also done at 1 hr and pupil diameter was measured, as previously described (14) at 0.5, 1, 3, 6 and 24 hr after drug application. These intervals were selected because previous studies have shown that IOP and pupillary diameter may be significantly or even maximally reduced 1 hr after topical PG application (13, 5) while flare and cellular responses were best assessed at 6 and 24 hr, respectively.

Flare and cellular response in the anterior chamber were both rated on the basis of slit-lamp biomicroscopic examination of the anterior chamber. The ratings for aqueous flare were: 0, no Tyndall effect; 0.5, slight Tyndall effect detectable only by a partially dark-adapted observer; 1+, slight but easily visible Tyndall effect; 2+, moderate to dense Tyndall effect; 3+, dense Tyndall effect with fibrin clots. Cellular response was rated as follows: 0, no cells; 0.5+, few cells observed upon scanning of most of the anterior chamber volume; 1+, some cells apparent in any given slitlamp field; 2+, numerous cells found in any given slitlamp field and 3+, cells densely dispersed or some cell clumps observed. The reasons for selecting these rating criteria rather than a rating system that has been advocated for use in toxicology has already been stated. (14)

Intraocular pressure (IOP) was measured on conscious animals, using a calibrated floating tip tonometer run on compressed oxygen (Pheumatonograph; Alcon, Fort Worth, Texas) after the topical application of one drop of 0.5% proparacaine HCL solution to provide corneal anesthesia. A more detailed description of the tonometric technique has been provided elsewhere. (14)

The contralateral control eye received either the same volume of vehicle solution or was untreated. The responses of the cats to the topical instillation of these solutions was assessed by noting behavioral responses, including the duration of lid closure. Overt behavioral responses such as vocalizations or escape attempts, which indicate severe discomfort, did not occur with any of the solutions used in this study.

$PGF_{2\alpha}$-IE and $PGA_2$-IE were supplied by Pharmacia, AB (Uppsala, Sweden) already dissolved in an ophthalmic vehicle solution containing 0.5% polysorbate 80 in saline. All dilutions were made with a similar vehicle that also contained 0.01% benzalkonium chloride. $PGA_2$ free acid was obtained from Cayman Chemical (Ann Arbor, Mich.) and was made up in ethanol and diluted to the needed concentration in the benzalkonium chloride vehicle solution. All solutions were delivered to the eye with an automatic micropiet (Eppendorf) set to deliver a volume of 25μl corresponding to 25.8±0.24 mg (10 determinations at 21° C.) of these solutions.

In one long-term experiment, first 0.5 μg of $PGF_{2\alpha}$-IE was applied once a day for 8 days. This was followed 24 hr after the last $PGF_{2\alpha}$-IE application by 3 months of treatment of the same eye with $PGA_2$-IE at a dose of 0.5 or 1.0 μg biomicroscopic examination of the eye were done on most working days between 8:14 and 9:00 AM (9 AM readings) before the application of the next PG dose and on most treatment workdays also at 1, 3 and 6 hr after treatment.

Results

Time curves of the intraocular pressure reduction obtained after the topical application of different doses of PGA$_2$-IE show that this PG ester can effectively reduce IOP in the dose range of 0.1 to 1.25 μg per eye (FIG. 9A). Maximum IOP reduction consistently occurs at 1 hr after the topical application of this drug and doses as low as 0.5 μg maintain significant IOP reduction at least up to 24 hr after application. This is in contrast to PGF$_{2\alpha}$-1-isopropyl ester (PGF$_{2\alpha}$-IE) that yielded a maintained IOP reduction throughout the first day of its topical application only at a dose of 1 μg, and only at a dose of 2.5 μg yielded an IOP reduction at 24 hr (FIG. 9B) that was comparable in magnitude to that observed after the topical application of 0.75 μg of PGA$_2$-IE.

Figure 10A:
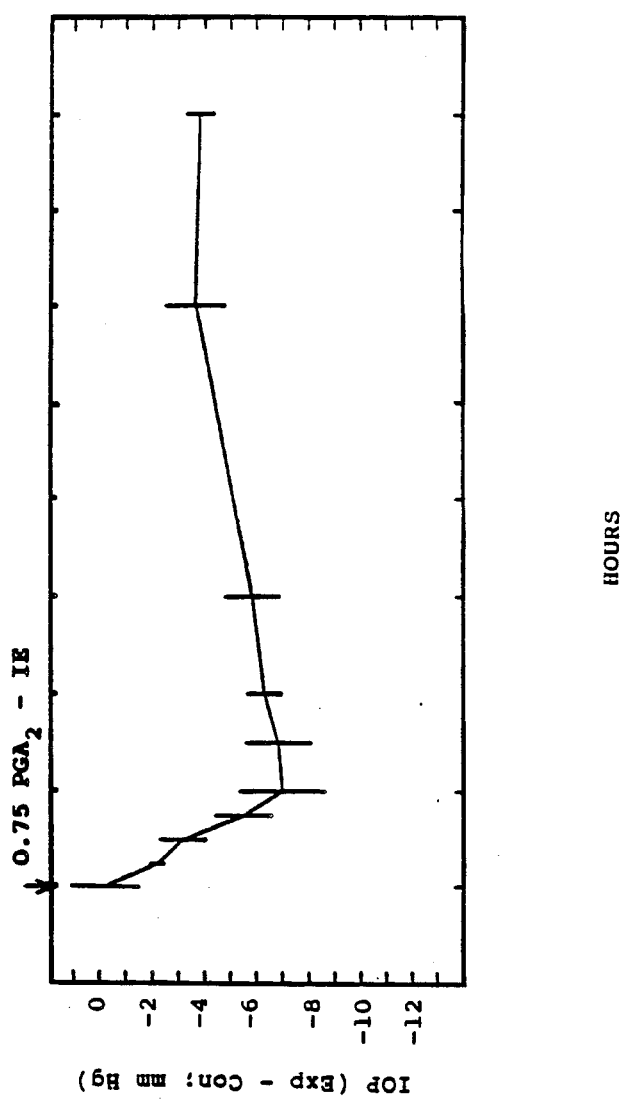
FIG. 10A. This figure shows the effect of topical application of 0.75 μg of PGA$_2$-IE on IOP in the cat eye. The IOP reduction in response to this topical application became significant at 30 minutes after its topical application and this IOP reduction was not preceded by an initial episode of increased IOP.
Figure 10B:
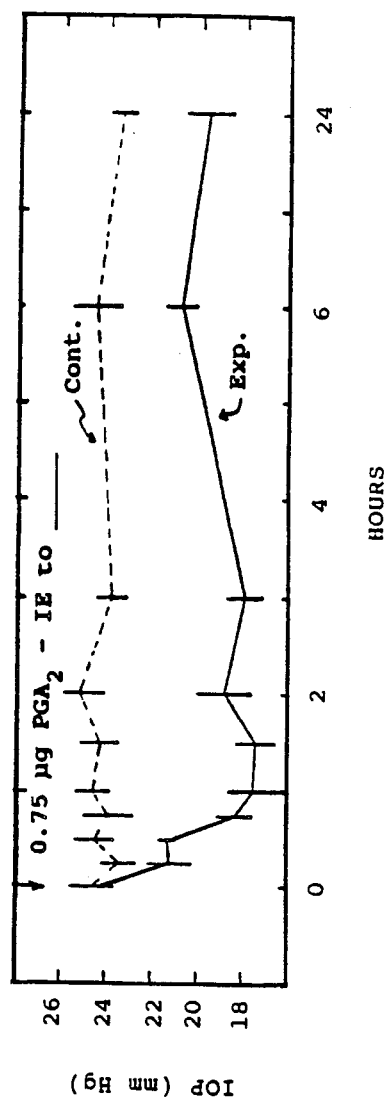
FIG. 10B. This figure shows that topical application of 0.75 μg of PGA$_2$-IE did not cause a significant IOP reduction in the contralateral control eyes of cats.

FIG. 10A shows that the IOP reduction in response to a topical application of 0.75 μg PGA$_2$-IE became significant at 30 minutes after its topical application and that this IOP reduction was not preceded by an initial episode of increased IOP which was previously found to occur after the topical application of some PGs, especially after the topical application of doses of PGE$_2$ sufficient to cause a similar IOP reduction. FIG. 10B shows that topical application of 0.75 μg of PGA$_2$-IE did not cause a significant IOP reduction in the contralateral control eye, demonstrating that the IOP reduction in the treated eye was not due to a systemic effect. In some previous studies, topical application of some PGs, especially unilateral topical application of PGF$_{2\alpha}$ to eyes of owl monkeys, was found to be associated with some IOP reduction in the contralateral eye.

Figure 11A:
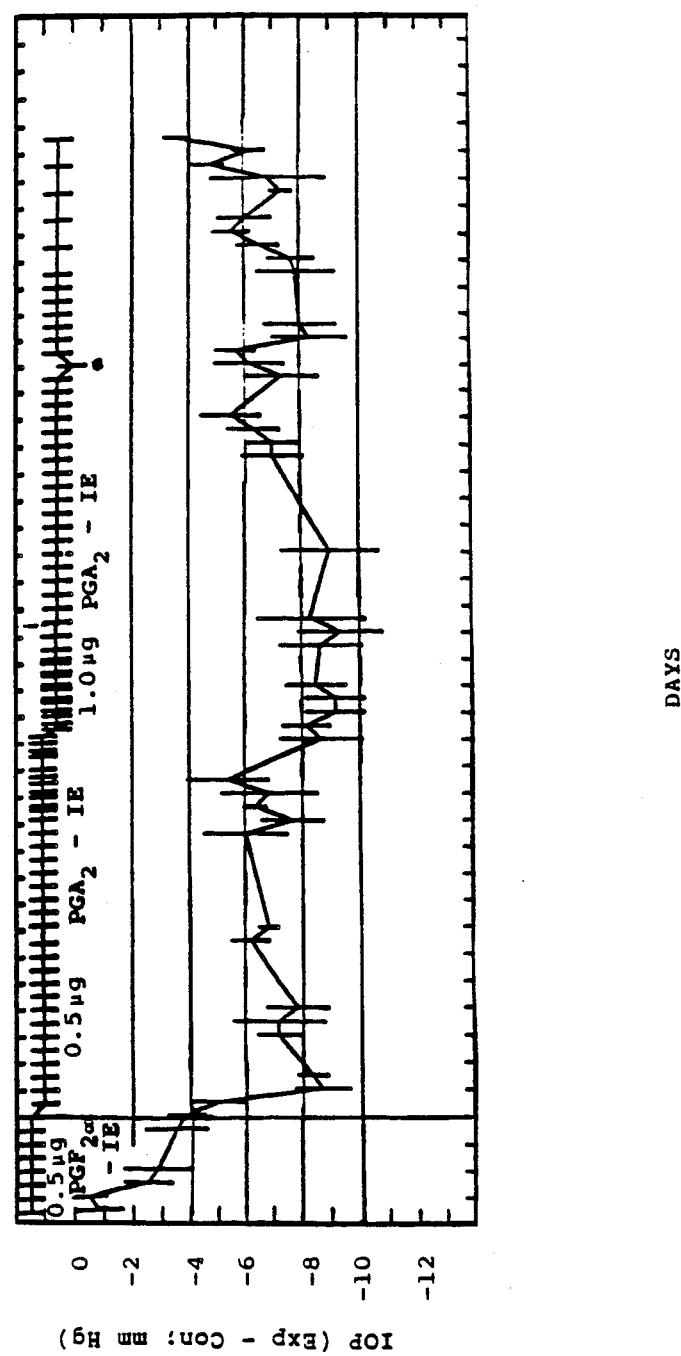
FIG. 11A. This figure shows the effect on IOP of the repeated application of 0.5 μg or 1.0μg of PGA$_2$-IE to one eye of a group of six ocular hypertensive cats. IOP reduction was increased over a period of 3-4 days after the beginning of the daily application of PGA$_2$-IE and then was maintained between 6-8 mm below the control eye as long as daily or every other day treatment was continued. The results demonstrate that PGA$_2$IE is able to maintain IOP reduction for 24 hr or even 48 hr during the course of long-term treatment. Each treatment is indicated by a vertical bar at the top of the figure.
Figure 11B:
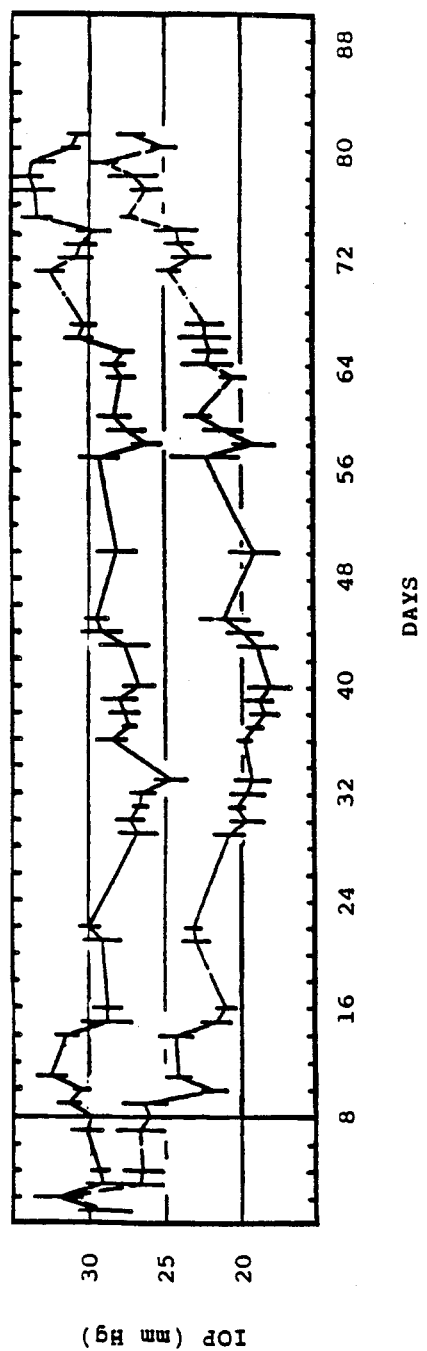
FIG. 11B. This figure shows the same data as presented in FIG. 11A except IOP values are given for the treated and control eye separately.

After the daily application of 0.5 μg of PGA$_2$-IE to one eye of a group of six ocular hypertensive cats, IOP reduction maintained for a full 24-hr period was greater than that obtained over a previous period of eight days of daily treatment of the same eyes with the same dose of PGF$_{2\alpha}$-IE. IOP reduction was increased over a period of 3-4 days after the beginning of the daily application of PGA$_2$-IE and then was maintained between 6-8 mm below the contralateral eye as long as daily treatment was continued (FIG. 11). Increasing the treatment from once a day to twice a day on the 31st day of treatment did not yield a further IOP reduction, indicating that once a day treatment with this PG ester is sufficient to maintain maximum IOP reduction. However, when the dose was increased from 0.5 μg per eye to 1 μg per eye on the 38th day of treatment, some enhancement of the IOP reduction was observed. When the frequency of treatment with 1 μg of PGA$_2$-IE was reduced from twice a day to once a day, only a very small portion of the IOP reduction was lost. When the frequency of treatment with 1 μg of PGA$_2$-IE was reduced from once a day to once every other day beginning with the 72nd day of treatment, highly significant IOP reduction was maintained even at 48 hr after each topical application of 1 μg of PGA$_2$-IE.

The results presented in FIG. 11 demonstrate that PGA$_2$-IE is able to maintain IOP reduction for 24 hr or even for 48 hr during the course of long-term treatment. These studies on the cat eye suggest that PGA$_2$-IE may be suitable for long-term treatment of glaucoma using once a day application of a relatively small dose and that such once a day treatment regimen will maintain effective IOP reduction even if one daily treatment is skipped occasionally as is expected to occur in the medical management of glaucoma because of lack of effective compliance.

All results demonstrate that PGA$_2$-IE is a most effective ocular hypotensive agent that is able to maintain IOP reductions over at least a 24-hr period even when applied topically to the eye at much lower doses than any other topically applied ocular hypotensive agents currently used in the practice of ophthalmology for the treatment of glaucoma.

References

1. Beitch, B. R. and Eakins, K. E. The Effect of Prostaglandins on the Intraocular Pressure of the Rabbit. Brit. Jour. Pharm 37(1): 158-167 (Sept. 1969).
2. Bito, L. Z. and Baroody, R. A.: The penetration of exogenous prostaglandin and arachidonic acid into, and their distribution within, the mammalian eye. Curr. Eye Res.1: 659-669 (1981/1982).
3. Bito, L. Z., Draga, A., Blanco, J., and Camras, C. B.: Long-term maintenance of reduced intraocular pressure by daily or twice daily topical applications of prostaglandins to cat or rhesus monkey eyes. Invest. Ophthalmol. Vis. Sci. 24: 312-319 (1983).
4. Bito, L. Z., Srinivasan, B. D., Baroody, R. A., Schubert, H.: Noninvasive observations on eyes of cats after long-term maintenance of reduced intraocular pressure by topical application of prostaglandin E$_2$. Invest. Ophthalmol. Vis. Sci. 24: 376-380 (1983).
5. Bito, L. Z.: Comparison of the ocular hypotensive efficacy of eicosanoids and related compounds. Exp. Eye. Res. 38: 181-194 (1984).
6. Chiang, T. S.: Effects of epinephrine and progesterone on the ocular hypertensive response to intravenous infusion of prostaglandin A2. Prostaglandins 4: 415-420 (1973).
7. Eliasson, R. and Brzdekiewicz, Z.: Tachyphylactic response of the isolated rat uterus to prostaglandins A. Pharmacol. Res. Comm. 1: 391-396 (1969).
8. Freas, W. and Grollman, S.: Uptake and binding of prostaglandins in a marine bivalve, *Modiolus demissus*. J. Exp. Zool. 216: 225-235 (1981).
9. Giuffre, G.: The efects of prostaglandins F$_2$ in the human eye. Graefes Arch. Clin. Exp. Ophthalmol. 222: 139-141 (1985).
10. Nakano, J., Chang, A. C. K. and Fisher, R. G.: Effects of prostaglandins E1, E2, A1, A2, and F2 on canine carotid arterial blood flow, cerebrospinal fluid pressure, and intraocular pressure. J. Neurosurg. 38: 32-39 (1973).
11. Stern, F. A. and Bito, L. Z.: A comparison of the hypotensive and other ocular effects of prostaglandin E$_2$ and F$_2$ on cat and rhesus monkey eyes. Invest. Ophthalmol. Vis. Sci. 22: 588-598 (1982).
12. Trzeciakowski, J. P., Chiou, F. Y., Watanabe, K. and Chiou, G. C. Y.: Effects of prostaglandins on intraocular pressure recovery rate in rabbits. Prostaglandins 29(3): 497-510 (March 1985).
13. Stern, F. A. and Bito, L. Z.: Comparison of the hypotensive and other ocular effects of prostaglandins E$_2$ and F$_2$ on cat and rhesus monkey eyes. Invest. Ophthal. Vis. Sci. 22: 588-598 (1982).
14. Bito, L. Z., Baroody, R. A and Miranda, O. C.: Eicosanoids as a new class of ocular hypotensive agents. 1. The apparent therapeutic advantages of derived prostaglandins of the A and B type as compared to primary prostaglandins of the E, F and D type. Exp. Eye Res. in Press. (1987).

What is claimed is:

1. A method for treating ocular hypertension or glaucoma in a subject's eye which comprises topically applying to the surface of the eye with an effective intraocular pressure reducing amount of prostaglandin A (PGA), prostaglandin B (PGB), or prostaglandin C (PGC), applied as the free acid form or as an ester so as to reduce the intraocular pressure of the eye and maintain such reduced intraocular pressure.

2. The method of claim 1, wherein the subject is an animal.

3. The method of claim 2, wherein the subject is a primate.

4. A method of claim 1, wherein the PGA is $PGA_1$, $PGA_2$ or $PGA_3$.

5. A method of claim 1, wherein the ester of PGA, PGB or PGC comprises an aliphatic or an arylalkyl ester at the 1-position or 15-position, or both, or PGA, PGB or PGC, respectively.

6. A method of claim 5, wherein the ester comprises an aliphatic diester at the 1-position and 15-position.

7. A method of claim 5, wherein the ester is an aliphatic ester at the 1-position or 15-position and is a methyl, ethyl, propyl or isopropyl ester.

8. A method of claim 5, wherein the ester is an arylalkyl ester at the 1-position or 15-position and is a benzyl ester.

9. A method of claim 1, wherein the amount of prostaglandin is in the range from about 0.1 microgram to about 500 micrograms.

10. A method of claim 9, wherein the amount of prostaglandin is in the range from about 0.1 microgram to about 50 micrograms.

11. A method of claim 1, wherein the PGB is $PGB_1$, $PGB_2$, or $PGB_3$.

12. A method of claim 1, wherein the PGC is $PGC_1$, $PGC_2$ or $PGC_3$.

13. A method of claim 1, wherein the contacting is repeated periodically.

* * * * *